United States Patent
Hassidov et al.

(10) Patent No.: US 11,511,034 B2
(45) Date of Patent: Nov. 29, 2022

(54) COLON EVACUATION WITHOUT COLLAPSE

(71) Applicant: Motus GI Medical Technologies Ltd., Tirat HaCarmel (IL)

(72) Inventors: Noam Hassidov, Moshav Bustan HaGalil (IL); Eyal Kochavi, Haifa (IL); Tzach Arnon, Yodfat (IL); Koby Luleko, Eshchar (IL); Mark Pomeranz, Bernardsville, IN (US)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 53 days.

(21) Appl. No.: 16/495,393

(22) PCT Filed: Mar. 19, 2018

(86) PCT No.: PCT/IL2018/050313
§ 371 (c)(1),
(2) Date: Sep. 19, 2019

(87) PCT Pub. No.: WO2018/173044
PCT Pub. Date: Sep. 27, 2018

(65) Prior Publication Data
US 2020/0093977 A1 Mar. 26, 2020

Related U.S. Application Data

(60) Provisional application No. 62/473,407, filed on Mar. 19, 2017.

(51) Int. Cl.
*A61M 3/02* (2006.01)
*A61M 13/00* (2006.01)
*A61B 1/31* (2006.01)

(52) U.S. Cl.
CPC ............... *A61M 3/022* (2014.02); *A61B 1/31* (2013.01); *A61M 3/0258* (2013.01);
(Continued)

(58) Field of Classification Search
CPC .. A61M 3/022; A61M 3/0283; A61M 13/003; A61M 3/0258; A61M 2205/3344;
(Continued)

(56) References Cited

U.S. PATENT DOCUMENTS

| 5,006,109 A | 4/1991 | Douglas et al. |
| 8,435,172 B2 | 5/2013 | Banik et al. |

(Continued)

FOREIGN PATENT DOCUMENTS

| CN | 102639168 | 8/2012 |
| CN | 103068419 | 4/2013 |

(Continued)

OTHER PUBLICATIONS

International Preliminary Report on Patentability dated Oct. 3, 2019 From the International Bureau of WIPO Re. Application No. PCT/IL2018/050313. (12 Pages).

(Continued)

*Primary Examiner* — Amber R Stiles
*Assistant Examiner* — Avery Smale

(57) ABSTRACT

Methods of colon cleansing and/or inspection are described which safely maintain a colon in an uncollapsed state. Balanced replacement of a volume of fluid, gas and/or solids evacuated during cleansing of the colon is described. Replacement volume comprises, for example, cleansing fluid, jetting gas, and/or inflation gas. In some embodiments, balancing of evacuated and replacement volume is achieved under automatic control, based on monitored volume of material exchange, and/or measurement of resulting pressures.

26 Claims, 7 Drawing Sheets

(52) U.S. Cl.
CPC ........ *A61M 3/0283* (2013.01); *A61M 13/003* (2013.01); *A61M 2205/3303* (2013.01); *A61M 2205/3344* (2013.01); *A61M 2210/1064* (2013.01)

(58) Field of Classification Search
CPC ........ A61M 1/0058; A61M 2205/3303; A61M 1/74; A61M 1/71; A61M 1/73; A61M 1/77; A61M 1/774; A61M 1/84; A61M 13/00; A61M 2202/068; A61M 2202/0225; A61M 1/772; A61M 2210/1064; A61M 3/0216; A61M 2025/0037; A61M 2205/50; A61M 1/80; A61M 1/85; A61M 2205/3331; A61M 2205/3334; A61B 1/31; A61B 1/015
See application file for complete search history.

(56) References Cited

U.S. PATENT DOCUMENTS

| | | |
|---|---|---|
| 2009/0306476 A1 | 12/2009 | Banik et al. |
| 2010/0185056 A1 | 7/2010 | Gordon et al. |
| 2010/0228222 A1* | 9/2010 | Williams ............ A61M 3/0208 604/500 |
| 2010/0268154 A1 | 10/2010 | Vining |
| 2011/0105845 A1 | 5/2011 | Gordon et al. |
| 2012/0101336 A1 | 4/2012 | Hirsch et al. |
| 2013/0085442 A1 | 4/2013 | Shtul et al. |
| 2013/0172805 A1* | 7/2013 | Truckai ............... A61M 3/0208 604/28 |
| 2015/0290403 A1 | 10/2015 | Torisawa et al. |
| 2016/0206805 A1 | 7/2016 | Hassidov et al. |

FOREIGN PATENT DOCUMENTS

| | | | |
|---|---|---|---|
| EP | 3082896 | 10/2016 | |
| EP | 3128893 | 2/2017 | |
| JP | 2013-532023 | 8/2013 | |
| WO | WO 2011/158232 | 12/2011 | |
| WO | WO 2015/029039 | 3/2015 | |
| WO | WO 2015/092790 | 6/2015 | |
| WO | WO 2015/155776 | 10/2015 | |
| WO | WO-2015193896 A1 * | 12/2015 | ............... A61B 1/31 |
| WO | WO 2018/173044 | 9/2018 | |

OTHER PUBLICATIONS

International Search Report and the Written Opinion dated Jul. 6, 2018 From the International Searching Authority Re. Application No. PCT/IL2018/050313. (17 Pages).

Supplementary European Search Report and the European Search Opinion dated Dec. 8, 2020 From the European Patent Office Re. Application No. 18770424.2. (6 Pages).

Notification of Office Action and Search Report dated Apr. 25, 2021 From the State Intellectual Property Office of the People's Republic of China Re. Application No. 201880028254.0 and Its Translation of Office Action Into English. (12 Pages).

Notice of Reasons for Rejection dated Mar. 8, 2022 From the Japan Patent Office Re. Application No. 2019-550242. and Its Translation Into English. (8 Pages).

* cited by examiner

COLON EVACUATION WITHOUT COLLAPSE

RELATED APPLICATIONS

This application is a National Phase of PCT Patent Application No. PCT/IL2018/050313 having International filing date of Mar. 19, 2018, which claims the benefit of priority under 35 USC § 119(e) of U.S. Provisional Patent Application No. 62/473,407 filed on Mar. 19, 2017. The contents of the above applications are all incorporated by reference as if fully set forth herein in their entirety.

FIELD AND BACKGROUND OF THE INVENTION

The present invention, in some embodiments thereof, relates to methods for clearing of fecal matter from a colon or other body lumen for diagnostic inspection, and, more particularly but not exclusively, to maintaining the colon in an uncollapsed state during cleaning and/or inspection.

A colonoscope provides means for optically and/or electronically imaging the colon and its contents, for example, to look for cancerous and/or pre-cancerous polyps. For effective viewing, a common practice before colonoscopy is to clear as much of a colon's contents as possible, sometimes by aggressive changes to diet and/or by administration of purgatives. In some methods of colon observation, imaging occurs while flushing or washing a portion of the colon with an irrigating fluid. Irrigating fluid, fecal matter and/or other colon contents are drawn out of the colon by suction and/or other methods for transporting matter out of the body. Colonoscopy is performed in a colon which is inflated. Inflation provides enhanced viewing and/or safety for navigation.

The following patent applications relate to the field of endeavor of the current application: U.S. Patent Application 2010/0185056 by Tal Gordon et al.; U.S. Patent Application 2011/0105845 by Tal Gordon et al.; and U.S. Patent Application 2012/0101336 by Yoav Hirsch et al.

SUMMARY OF THE INVENTION

There is provided, in accordance with some embodiments of the present disclosure, a colon cleaning system for evacuating material from a distal end of a colon while keeping the colon in a safely inflated state allowing internal observation, the colon cleaning system comprising: an evacuation conduit having a distal region insertable to the colon to communicate suction for evacuating the material; an insufflation conduit for supply of insufflation gas to inflate the colon; a controller; and a pressure sensor configured to provide pressure measurements from the distal region to the controller; wherein the controller is configured to regulate a flow of the supply of insufflation gas and the suction to produce and maintain the inflated state, based on the pressure measurements.

In some embodiments, the system comprises a sensor configured to measure a relative proportion of gas in an evacuated mixture of at least gas and liquid evacuated through the evacuation conduit; and wherein the controller is also configured to adjust the supply of insufflation gas, based on the relative proportion of gas in the evacuated mixture of at least gas and liquid.

In some embodiments, the distal region comprises a connector which attaches to a colonoscope for insertion to the distal end of the colon.

In some embodiments, the controller is configured to regulate the flow to keep measurements from the pressure sensor within a predetermined range of pressures consistent with the safely inflated state allowing internal observation.

In some embodiments, the predetermined range of pressures comprises upper and lower bounds both between 5 mbar and 40 mbar above ambient pressure.

In some embodiments, the supply of insufflation gas is increased based on decreasing value of the pressure measurements.

In some embodiments, the supply of insufflating gas is variable by the controller to multiple different supply rates and/or pressures as the pressure measurements change.

In some embodiments, the increase comprises increase in the rate of supply of the insufflation gas.

In some embodiments, the increase comprises increase in the duration of supply of the insufflation gas.

In some embodiments, the suction is decreased based on decreasing value of the pressure measurements.

In some embodiments, the suction decrease comprises decrease in the magnitude of the suction pressure.

In some embodiments, the suction decrease comprises decrease in the duration of supply of the suction pressure.

In some embodiments, the predetermined range of pressures is adjustable during use.

In some embodiments, the controller is configured to initiate suction upon receipt of an operator command.

In some embodiments, the controller is configured to increase the supply of insufflation gas upon initiation of suction.

In some embodiments, the colon cleaning system comprises an irrigating conduit, attachable to an irrigating fluid supply; and the flow regulated by the controller to maintain the inflated state also includes the supply of irrigating fluid from the irrigating fluid supply to the irrigating conduit.

In some embodiments, the controller is configured to reduce the supply of insufflating gas as a function of an increase in the supply of irrigating fluid.

In some embodiments, the reduction of the supply of insufflating gas is variable by the controller to multiple different supply rates and/or pressures as the supply of irrigating fluid increases.

In some embodiments, the controller is configured to initiate supply of irrigating fluid upon receipt of an operator command.

In some embodiments, the controller is configured to decrease the supply of insufflation gas upon initiation of irrigating fluid supply.

In some embodiments, the controller is configured to increase the supply of suction upon initiation of irrigating fluid supply.

In some embodiments, the controller responds to an acceleration in a rate of decrease in the pressure measurements by commanding a larger supply of insufflation gas than is needed to counteract the current rate of decrease in pressure.

In some embodiments, the colon cleaning system is provided together with a colonoscope.

In some embodiments, the evacuating conduit is attached to a positive displacement pump providing the suction for evacuating the material.

In some embodiments, the controller is configured to maintain the inflated state of the colon, based on an estimated volume of material removed by suction from colon by the positive displacement pump.

In some embodiments, the estimated volume is based on a speed of operation of the positive displacement pump.

In some embodiments, the estimated volume is based on power consumption by the positive displacement pump.

There is provided, in accordance with some embodiments of the present disclosure, a method of operating a device to safely maintain a safely inflated state of a colon allowing internal observation during colon cleaning, the method comprising: evacuating material including fluid from the colon through a distal aperture of an evacuation conduit of the device inserted to a distal region of the colon, wherein the material is evacuated by suction supplied to the distal aperture; sensing with a pressure sensor of the device a change in pressure measured within the distal region due to the evacuation of material; and controlling, using a controller of the device, a supply of insufflating gas delivered to the colon from an insufflation conduit of the device, wherein the amount of insufflating gas supply is determined automatically by the controller based on the sensed change in pressure.

In some embodiments, the method comprises adjusting the supply of insufflation gas, based on a relative proportion of gas in the evacuated mixture of at least gas and liquid.

In some embodiments, the amount of gas supplied from the insufflation conduit is also controlled by the controller based on an estimate of the amount of the material removed by a current rate of suction.

In some embodiments, the estimate of the amount of material removed is based on a volume of material removed by a positive displacement pump.

In some embodiments, the method further comprises supplying irrigation fluid to the colon during the evacuating material.

In some embodiments, the amount of gas supplied from the insufflation conduit is also based on an estimate of the amount of irrigation fluid supplied.

In some embodiments, relative magnitude of the rate of supply of insufflation gas compared to a magnitude of evacuation pressure supply is automatically increased as the measured pressure decreases.

In some embodiments, the relative magnitude of the rate of supply of insufflation gas compared to a magnitude of evacuation pressure supply is automatically increased by the controller through a range of multiple different values, based on the decrease in measured pressure.

In some embodiments, relative magnitude of the rate of supply of insufflation gas compared to a magnitude of evacuation pressure supply is automatically decreased as the measured pressure increases.

In some embodiments, the relative magnitude of the rate of supply of insufflation gas compared to a magnitude of evacuation pressure supply is automatically decreased by the controller through a range of multiple different values, based on the increase in measured pressure.

In some embodiments, the changes to relative magnitude of insufflation gas and evacuation pressure supply are chosen to maintain the measured pressure within a predetermined pressure range.

In some embodiments, the magnitude of evacuation pressure supply comprises one or more of an applied evacuation pressure magnitude or a duration of applied evacuation pressure.

There is provided, in accordance with some embodiments of the present disclosure, a colon cleaning system for evacuating material from a distal end of a colon while keeping the colon in a safely inflated state allowing internal observation, the colon cleaning system comprising: an evacuation conduit having a distal region insertable to the colon to communicate suction for evacuating the material; an insufflation conduit for supply of insufflation gas to inflate the colon; an irrigating conduit, for supply of irrigating fluid to irrigate the colon; a controller; and a pressure sensor configured to provide pressure measurements from the distal region to the controller; wherein the controller is configured to regulate a net flow of at least two of the supply of insufflation gas, the supply of irrigating fluid, and the suction to produce and maintain the inflated state, based on the pressure measurements.

In some embodiments, the system comprises a sensor configured to measure a relative proportion of gas in an evacuated mixture of at least gas and liquid evacuated through the evacuation conduit; and the controller is also configured to adjust the supply of insufflation gas, based on the relative proportion of gas in the evacuated mixture of at least gas and liquid.

There is provided, in accordance with some embodiments of the present disclosure, a method of detecting blockage in an evacuation lumen of a colon cleaning system, comprising measuring a pump cycling rate of a positive displacement pump used to provide suction to the evacuation lumen, and providing an indication of blockage, based on the pump cycling rate.

There is provided, in accordance with some embodiments of the present disclosure, a method of detecting blockage in an evacuation lumen of a colon cleaning system, comprising measuring power consumption by a positive displacement pump used to provide suction to the evacuation lumen, and providing an indication of blockage, based on the measured power consumption.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
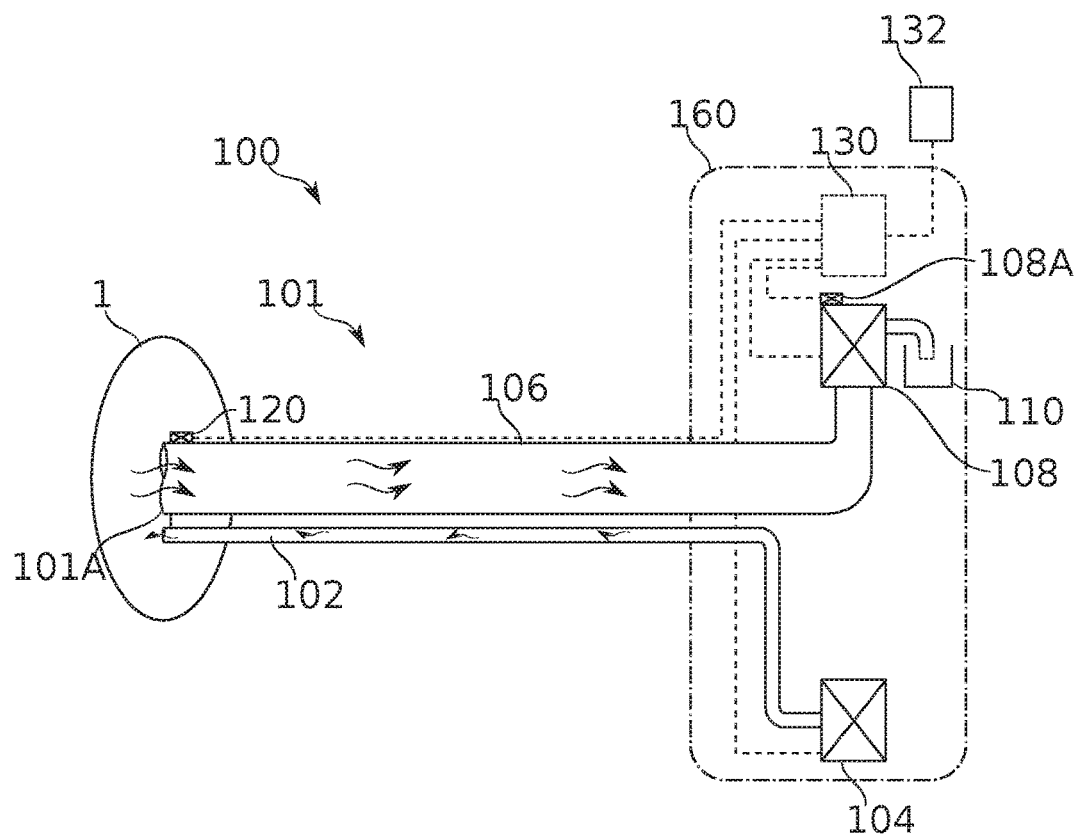
FIG. 1A is a schematic drawing of a colon cleansing system comprising insufflating apparatus for automatic maintenance of a non-collapsed colon state, according to some exemplary embodiments of the invention.

The present invention, in some embodiments thereof, relates to methods for clearing of fecal matter from a colon or other body lumen for diagnostic inspection, and, more particularly but not exclusively, to maintaining the colon in an uncollapsed state during cleaning and/or inspection.

Overview

A broad aspect of some embodiments of the invention relates to the maintenance of inflation state in a large intestine during operations to evacuate fecal material.

In some embodiments of the invention, an automatically operating insufflation subsystem is provided with a colon cleaning system for improved management of colon inflation state.

In some embodiments, operation of a colon cleaning system involves the flux of matter into and out of the colon. In some embodiments, fluid (liquid and/or gas) is introduced to, and/or liquid, gas, and/or solids are evacuated from the colon at a distance corresponding to an insertion distance of an irrigation and/or evacuation conduit of the colon cleaning system. Optionally, the insertion distance is up to at least 50%, 75%, or substantially an entire length of the colon (for example, reaching to the cecum of the colon); and/or up to at least 1 meter, 1.2 meters, 1.4 meters, or 1.6 meters. Irrigation fluid is introduced to break apart, loosen, suspend and/or dissolve fecal matter. The irrigation fluid and fecal matter are evacuated through a lumen of an evacuation conduit. Cleaning is performed, in some embodiments, along with viewing through a colonoscope, used to inspect the colon for lesions such as cancerous and/or precancerous growths on the colon wall.

Colonoscopy, with or without use of a colon cleaning system, typically involves inflation of the colon. In the course of a typical colonoscopy, the colon is inflated with gas (insufflated) as part of the procedure. Gas inflation holds the colon in an open position, potentially assisting navigation of a colonoscope probe and/or providing a clearer view of the intestinal wall. Contrariwise, a collapsed colon presents a potential hazard for the procedure, wherein the advancing or retreating colonoscope probe potentially pushes and/or pulls against the tissue of a collapsed constriction with sufficient force to cause damage (e.g., perforation). Moreover, even when collapse is noticed in a timely fashion, there may still be a period of waiting and/or distraction from the main procedure while re-inflation occurs. Overinflation is also a potential danger.

Colon inflation state, during use of a colon cleaning system, is subject to several potential dynamic effects, including effects due to operation of the cleaning system itself. There can be leakage of insufflating gas from the colon, and/or transfer of insufflation pressure between compartments of the colon, for example, compartments which form due to pinching that restricts the passage of gas between the ascending, transverse, and/or descending colon. Irrigation fluid (comprising liquid and/or gas) acts to further inflate the bowel. Evacuation tends to deflate the bowel. Use of an intra-colon cleaning system can potentially greatly increase flux of material into and out of a colon compared to material flux during a standard colonoscopy, potentially increasing the difficulty of achieving a safe balance of the two. For example, evacuation, though typically targeted at removal of fluids and solids, potentially extracts gas which is part of the volume supplied for inflation, e.g., when an intake aperture is not fully immersed in irrigation fluid.

Insufflation gas to remedy imbalance is optionally supplied manually at intervals to remedy this imbalance, but doing so may require exercising judgment about the inflation state of the colon. There is risk of error on least two sides. The rate of evacuation (and/or escape of gas, e.g., via the anus) overtaking the introduction of irrigation and/or insufflation material may lead to underinflation and colon collapse. In contrast, if evacuation rate is slowed relative to the supply of irrigation and/or insufflation, overinflation potentially occurs, increasing risk of a rupture or other dangerous situation.

An aspect of some embodiments of the invention relates to insufflation of an intestine simultaneously with evacuation and/or irrigation.

In some embodiments, a conduit dedicated to colon insufflation is provided in a cleaning system probe. Although insufflation and irrigation are optionally performed, in some embodiments, by a single conduit (switched between gas and liquid as needed), it is a potential advantage to provide a dedicated supply conduit for each of insufflation and irrigation. In particular, this potentially allows specialization of the two conduits, since, for example, irrigation is advantageously performed in some embodiments using jets of fluid passed through specialized and/or aimed outlet apertures. Furthermore, it is a potential advantage for both insufflation and irrigation to occur during evacuation, with insufflation volume being supplied, in some embodiments, to replace the volume which is evacuated, but not re-supplied by simultaneous irrigation.

In some embodiments, a supply aperture of an insufflation tube is positioned longitudinally nearby distal apertures for evacuation and/or irrigation (for example, longitudinally within 1 cm, 5 cm, 10 cm, 20 cm, or another larger smaller or intermediate distance). Potentially this helps to ensure that added and removed volumes are balanced within a working compartment. In some embodiments, the supply aperture is also positioned near a pressure sensor configured to sense pressure within the colon.

An aspect of some embodiments of the invention relates to use of a sensor to determine a state of inflation of a colon.

In some embodiments of the invention, remote sensing is used to determine an aspect of a colon inflation state. Optionally, this state is used as a basis for determining whether to insufflate the colon further. In some embodiments, the determination is automatic.

In some embodiments, remote sensing comprises pressure sensing, for example, sensing of pressure in the colon at a site of irrigation and/or insufflation material delivery. Optionally, the system is configured to maintain a sensed pressure set point or range.

In some embodiments, remote sensing comprises another sensing means, for example, imaging. In some embodiments, sensing used as a basis for insufflation determination comprises direct information about matter flux, for example, data about commanded operation of insufflation, irrigation and/or evacuation supplies of pressure and/or material. In some embodiments, a rate of matter passing through the system is sensed and used for determinations about colon inflation state.

In some embodiments, a plurality of information sources is used to determine a state of inflation of the colon. For example, a cleaning system is configured (for example, calibrated, and/or by balancing sensed and/or commanded transfer of material) to supply insufflation gas and/or irrigation fluid in a substantially equal amount to the commanded volume of material suctioned from the cleaning system. Excursions from the static state which should be maintained by this calibration (due, for example, to leakages, compression, transfers of material within the colon, and/or irrigation) are optionally corrected by sensing of pressure, and supplying insufflation gas, fluid, and/or suction pressure to compensate for changes.

In some embodiments, a relative amount of gas compared to other material in the colon is sensed by a sensor, and/or determined by a controller based on sensing, optionally in addition to pressure sensing. In some embodiments, material evacuated through an evacuation channel is monitored to sense relative volumes of liquid and gas being evacuated. The sensing may comprise, for example, comparing a weight and/or volume of liquid (optionally including liquid-suspended solids) evacuated to a total volume of fluid (gas, liquid, and solids) evacuated. In some embodiments, liquid and/or gas delivery to the colon (e.g., by on or more irrigation and/or insufflation channels) is monitored by sensing and/or based on recording amounts (e.g., weights and/or volumes) of material commanded to be delivered under the control of a controller. An aspect of some embodiments of the invention relates to the automatic adjustment of colon inflation state, based on sensed data and/or an automatic determination of inflation state based on sensed data.

In some embodiments, a controller commands the operating parameters of one or more pressure and/or matter supplies based on an inflation state determination. Optionally, the determination to insufflate includes determining at what rate and/or with how much gas. In some embodiments, operation parameters are adjusted to change the expected reading of a pressure sensor. In some embodiments, a target pressure range for colon inflation is within 5 mbar to 40 mbar above atmospheric pressure. In some embodiments, a preferred target pressure is set to a single pressure, and/or a narrow range of pressures, for example, 5 mbar, 10 mbar, 15 mbar or 20 mbar, or another greater, lesser, or intermediate pressure, with a tolerance around a target pressure of ±1 mbar, ±2 mbar, ±5 mbar, ±8 mbar, or another greater, lesser or intermediate tolerance value. In some embodiments, a tolerance above a target pressure is greater or smaller than a tolerance below a target pressure.

In some embodiments, inflation pressure is actively adjusted when it falls below a target pressure, for example, by increasing a rate of insufflation and/or decreasing a rate of evacuation. In some embodiments, pressure above a target pressure is handled without immediate attention, particularly if it is not too far above that pressure for safety: for example, allowed to reduce naturally and/or as a function of ongoing evacuation activities. This is a potential advantage, for example, to reduce repeated on/off cycling of an insufflation supply. In some embodiments, ongoing evacuation activities are adjusted upon their normal activation: for example, evacuation commands are adjusted in suction power and/or in length of activation time when they are issued to the system, optionally by one or both of the controller and a user-initiated command. In some embodiments, a pressure above a target pressure is actively reduced. For example, evacuation is activated automatically to reduce pressure, and/or evacuation is modified to increase the amount of material evacuated, such as by increasing the magnitude of the evacuation pressure differential (suction) and/or the duration over which it is active. In some embodiments, actions to restore a target pressure are graded, for example, made stronger at pressures further away from a target pressure.

In some embodiments, material delivered to maintain inflation of the colon is selected to be a gas, liquid, and/or a mixture of the two, in proportions selected to maintain a safe and uncollapsed inflation state of the colon, while also maintaining a level of liquid in the colon, e.g., at least a 5%, 10%, 15%, 20%, or 25% full level of liquid (by volume) in an otherwise gas-inflated colon. Additionally or alternatively, in some embodiments, fluid irrigation is optionally restricted (in favor of gas insufflation) to avoid over-filling a colon with liquid, for example, to reduce a level of liquid in the colon to below a 10%, 15%, 20%, 25% or 30% full level of liquid (by volume) in an otherwise gas-inflated colon. In some embodiments, a targeted liquid filling range is between 5%-20% full of liquid, 10%-30%, 5%-35%, or another filling range. In some embodiments, sensed pressure measurements are used along with sensed and/or monitored movements of material into and/or out of the colon in order to determine what proportion of liquid and gas is to be delivered by irrigation and/or insufflation for creating and/or maintaining a targeted state of colon inflation as well as a targeted state of relative liquid and/or gas in the inflated colon.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Insufflating Colon Cleaning System

Figure 1B:
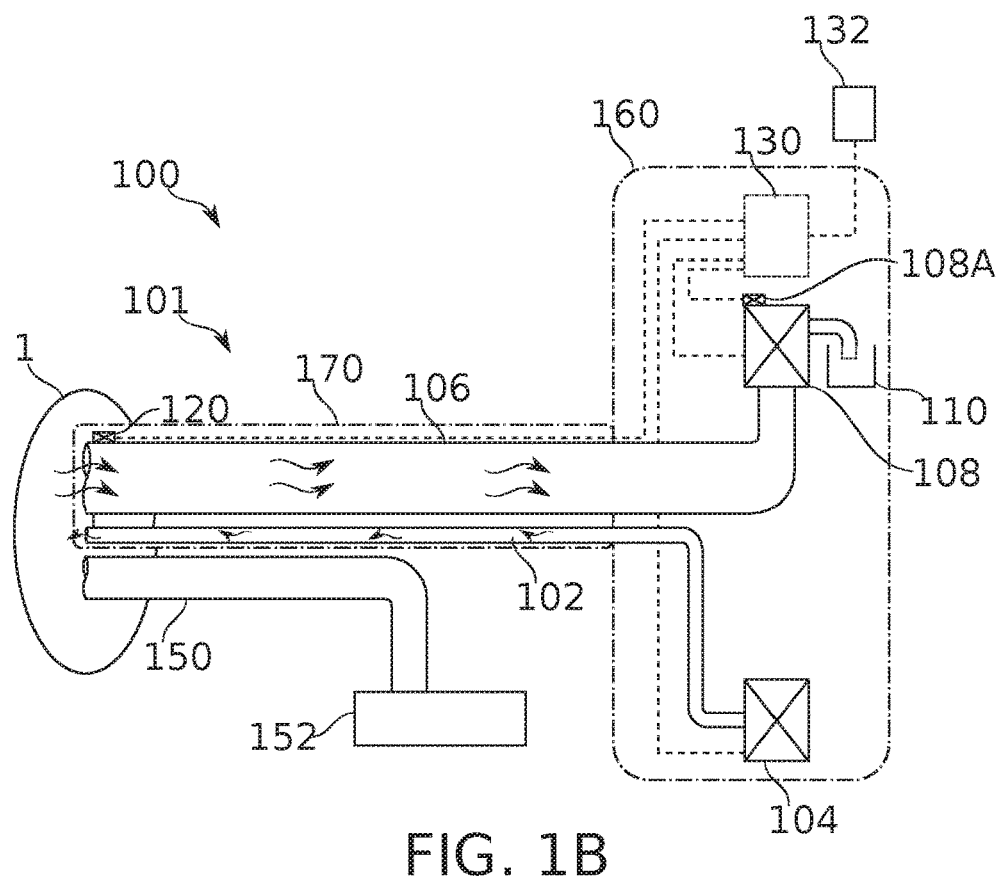
FIG. 1B is a schematic drawing of a colon cleansing system comprising insufflating apparatus for automatic maintenance of a non-collapsed colon state, along with an attached colonoscope, according to some exemplary embodiments of the invention.

Reference is now made to FIG. 1A, which is a schematic drawing of a colon cleansing system comprising insufflating apparatus for automatic maintenance of a non-collapsed colon state, according to some exemplary embodiments of the invention. Reference is also made to FIG. 1B, which is a schematic drawing of a colon cleansing system comprising insufflating apparatus for automatic maintenance of a non-collapsed colon state, along with an attached colonoscope, according to some exemplary embodiments of the invention. Further reference is made to FIG. 2, which is a schematic drawing of a colon cleansing system comprising insufflating apparatus for automatic maintenance of a non-collapsed colon state and a separate irrigating subsystem, according to some exemplary embodiments of the invention.

In some embodiments of the invention, an insufflation subsystem provided with a colon cleaning system is configured for improved management of colon insufflation.

In some embodiments of the invention, a colon cleaning system 100 comprises a probe 101, sized and configured for insertion from the anus to reach the distal (internally deepest, e.g., up to a cecum) end of a large intestine 1. The probe 101, in some embodiments, includes a gas pressure delivery tube (insufflation tube) 102 extending to an aperture at the distal end 101A of the probe 101. In some embodiments, cleaning system 100 comprises a gas source 104 (e.g., pumped gas, compressed gas from a tank, and/or facility-supplied gas such as from a wall outlet) configured to supply an insufflating gas through insufflation tube 102. In some embodiments, the material moved by gas source 104 comprises $CO_2$, air, or another gas. Optionally, gas source 104 comprises a peristaltic pump, and/or a valve.

In some embodiments, the colon cleaning system 100 comprises an evacuation conduit 106 extending to the distal end 101A of probe 101, and attached at the other end to cleaning system base station 160. An evacuation pressure source 108 is configured to apply suction to an evacuation conduit 106, such that material in the colon 1 near the distal end 101A of the probe 101 is evacuated therethrough. Evacuation pressure source 108 comprises, for example, a pump; and/or a vacuum source attached to through a wall outlet.

In some embodiments, pressure source 108 comprises a positive displacement pump such as a peristaltic pump or other positive displacement pump design (e.g., a rotary or reciprocating positive displacement pump). As evacuation proceeds, an intake aperture at a distal end 101A of probe 101 may be at different times fully immersed in liquid, fully exposed to gas, and/or positioned at any intermediate stage of liquid/gas exposure. There may also be partial blockage of the intake aperture, e.g., by tissue and/or waste solids material. If pressure source 108 operates by imposing a substantially constant pressure differential between distal end 101A and base station 160 (e.g., as for suction from a wall vacuum outlet), then there can be large volumetric variations in evacuation volume per unit time as the relative liquid/gas exposure of the intake aperture changes. This can be due, for example, to liquid/gas differences in viscosity and/or mass.

Positive displacement pumps, in contrast, operate to transport substantially constant-volume amounts as a function of operating cycle. The material volume actually extracted at a source per pump cycle may be somewhat different for liquid and gas materials (e.g., due to differences in their compressibility), but still potentially more stable with respect to materials of different viscosity than source volume extracted by a constant-pressure source.

A potential advantage of using a positive displacement pump in particular is to help preserve a more consistent relationship between controller commands and evacuation results. Such a relationship is used by the controller 130, in some embodiments, to more accurately predict commanded effects of pump operation on pressure, potentially reducing operating speed oscillations and/or pressure undershoot/overshoot. Moreover, sudden variations in evacuated volume (e.g., due to changes in transported material viscosity) can cause corresponding fluctuations in pressure that may be difficult to distinguish from other causes, e.g., leaks. With a positive displacement pump, effects on intra-colon pressure readings due to volume removal may be easier to compensate for, e.g., by assuming a substantially linear relationship between pump cycles and volume removed. With reduction in the numbers and/or risk of colon collapsing potentially occurring with more certain control results, the overall time of the procedure is also potentially reduced. The reduction can be, for example, because the actual occurrence of collapses is lowered, and/or because less extreme caution (e.g., smaller "buffers" in the target pressure range, and/or a larger rate of pressure change allowable) is needed to avoid overshooting and/or undershooting intra-colon pressure targets.

Optionally, evacuated material is deposited in a waste receiving container 110. In some embodiments of the invention, a dedicated irrigation conduit 202 is provided, supplied with gas, liquid, and/or a mix thereof from an irrigation source 204.

For clarity of exposition, the descriptions herein generally relate to the functions of insufflation, evacuation, and irrigation as performed by distinct structures. Provision of distinct structure for each function provides the potential advantage of allowing simultaneous performance of each function. Another potential advantage is to allow a greater degree of functional specialization in each structure, as described hereinbelow. However, it is to be understood that the functions are combined and/or shared among structures (for example, conduits and/or pressure sources) in some embodiments. In some embodiments, for example, roles of irrigation conduit 202 and insufflation conduit 102 are performed by a single insufflation/irrigation conduit 102, wherein determination of the role played at a given time comprises the selection of gas, liquid and/or a gas-liquid mix. Optionally, a gas-liquid mix is in a specified ratio. In some embodiments, roles of insufflation and irrigation are shared alternately and/or simultaneously among two or more supply conduits 102, 202. Additionally or alternatively, pressure source 108 attached to an evacuation conduit 106 is optionally reversible to comprise a supply conduit for liquid and/or gas, for performing irrigation and/or insufflation roles. Potentially, such combinations result in reduced complexity and/or size of a colon cleaning system.

Considering, conversely, benefits of greater structural specialization, there are optional differences between insufflation and irrigation and/or evacuation subsystems of a cleaning device which make them potentially less well-suited for interchangeable operation.

An irrigation source (including, for example, liquid and/or gas supply, conduit, and/or introducing aperture), in some embodiments, is configured for particular requirements of cleaning action. For example, the irrigation outlet, in some embodiments, comprises one or more apertures configured to shape and/or direct jets to assist in cleaning. An irrigation outlet, in some embodiments, is configured to work with liquid, and/or with a mix of liquid and gas. In some embodiments, a liquid/gas mix is selected for its cleaning properties, for example, to transfer energy to fecal matter to break it apart. Such specializations potentially impede use of a conduit as a dedicated insufflation conduit, by restricting the rate of volume introduction, increasing nozzle velocity, and/or enforcing a particular placement of an insufflation aperture. Modification to allow an irrigation conduit to introduce a pure gas mixture as desired potentially increases complexity at the pressure source.

In some embodiments, a mode of operation of a colon cleaning system comprises operation (while a colon remains safely inflated) within a targeted range of liquid filling of the colon (optionally, a particular part of the colon, for example, a cecum, an ascending, transverse, and/or descending segment of the colon, a sigmoid colon, and/or a rectum). Optionally, the targeted range corresponds, for example, to at least 5%, 10%, 15%, 25%, 30%, or another liquid filling fraction level (e.g., by volume). Additionally, or alternatively, the targeted range of liquid filling of the colon is less than, for example, 10%, 15%, 25%, 30%, 35% or another liquid filling fraction level (e.g., by volume).

An evacuation conduit, in some embodiments, comprises a comparatively large-diameter tube, in order to evacuate solid and/or liquid waste rapidly, without excessive clogging. The length and diameter of the evacuation conduit thus comprise a substantial "dead volume", preventing it from being used for gaseous insufflation until the dead volume is first purged. This makes it potentially inconvenient as a primary insufflation source, since there is built-in lag for switching between evacuation and insufflation function, in addition to the lack of capacity for simultaneous evacuation and insufflation through such a tube.

In some embodiments of the invention, a pressure sensor 120 is provided at a colon-inserted region of probe 101. In some embodiments, the pressure sensor 120 is provided at the distal end 101A of the probe. The pressure sensor 120 is configured to sense changes in pressure external to the probe, for example by placement on the outside of the probe.

Measured pressure, in some embodiments, is used in determining the current insufflation state of the colon. The inventors have found that an inflation pressure of about 5 mbar above atmospheric pressure is typically sufficient to maintain a non-obstructing inflation state. An upper range of desirable inflation pressure is about 40 mbar. The sensor is advantageously configured to measure pressures at least within this range. Herein, pressures provided are gauge pressures, expressed relative to atmospheric pressure, unless otherwise indicated.

Additionally or alternatively, in some embodiments, a pressure sensor 120 is provided at one or more other points along probe 101. For example, a pressure sensor 120 is provided along the length of the probe, about every 100 cm, 50 cm, 20 cm, with another greater, lesser or intermediate spacing, and/or with an irregular spacing. In some embodiments, sensors near the distal end 101A of the probe 101 are positioned pressure in a colon compartment which is directly subject to insufflation, evacuation, and/or irrigation. In some embodiments, more proximal sensors potentially sense a different pressure; for example, a pressure in a more proximal compartment of the colon. Potentially, the colon is separated into compartments experiencing different pressures, for example due to constrictions along the length of the intestine due to peristalsis and/or the normal geometry of the colon. For example, the descending, transverse and/or ascending colon potentially comprise compartments at least intermittently separated by constrictions at the left and/or right colic flexures. In some embodiments, pressure sensors distributed along the length of the colon provide information about the distribution of insufflation gas throughout the colon. In some embodiments, pressure sensors in different locations allow distinctions to be made which rule out transient and/or spurious sensor readings, for example, due to wall contact and/or sensor malfunction.

In some embodiments, a reservoir constant pressure is developed at a gas source 104, and vented to the colon through insufflation tube 102. This provides a potential advantage by allowing sensing to be contained outside the body. However, the indirect nature of the sensing, and the potential for blockage and/or blow-back from the contaminated environment indicate potential advantages for placing a sensor 120 within the cavity of the colon itself.

In some embodiments of the invention, a controller 130 is provided which commands the operation of pressure supplies 108, 104, 204 and/or other pressure supplies, and/or valves, on the basis of received information from pressure sensor 120 and/or one or more other sensors. Without variable control (e.g., among three or more (multiple) insufflation pressures and/or rates, and optionally among substantially continuously selectable insufflation pressures and/or rates), it is potentially difficult to match rates of evacuation and irrigation volume in order to safely maintain a non-collapsed colon. One reason for this, in some embodiments (e.g., embodiments using constant-pressure evacuation) is that the intake aperture of an evacuation conduit, for example, can be in liquid, in gas, partially in either, and/or partially blocked. The rate of evacuation is different in each state; for example: slower in liquid (due, for example, to higher mass and/or viscosity), and/or faster in gas. Thus there may be no single irrigation and/or insufflation rate which matches the volume evacuated at a given suction pressure (evacuation supply pressure) applied to an evacuation conduit.

Nevertheless, in some embodiments, an approximate calibration between commanded and/or measured volumes of introduced and evacuated material allows at least partial control without feedback, for example, from direct sensing of conditions within the colon. In some embodiments, a positive displacement pump is used to transport material; this potentially increases the accuracy with which such a calibration can be applied. Optionally, sensing within the colon is used to correct errors in the approximate calibration.

In some embodiments, sensing comprises sensing of operating characteristics of a pressure supply 108 itself. In particular, a pump (e.g., a positive displacement pump) may undergo changes in operating speed (e.g., pump cycles/second) and/or power consumption (e.g., electrical consumption) in response to changes in evacuation load, which changes are sensed (e.g., by sensor 108A) and provided to the controller 130.

In some embodiments, speed changes of a positive displacement pump (e.g., due to load increase/decrease) area measured (e.g., by use of an encoder as sensor 108A, or another measurement method). Optionally, the measured result is used by the controller 130 to modify an estimate of the volume of material being extracted under currently existing conditions. Optionally, the sensed change in speed is calibrated to an associated relative gas/fluid ratio. In some embodiments, this calibration is used by the controller to estimate, based on pump speed, how much gas and how much fluid has been evacuated. Optionally, the controller selects a ratio between supply of gas insufflation and supply of liquid irrigation, based on the measured ratio of their evacuation.

Additionally or alternatively to pump speed, pump power consumption is measured. For example, in some embodiments, an ammeter is used as sensor 108A to measure pump electrical power consumption. As described for pump speed (and changed as necessary), power consumption measurement is optionally used to estimate total and/or relative gas/liquid evacuation volumes.

Figure 7:
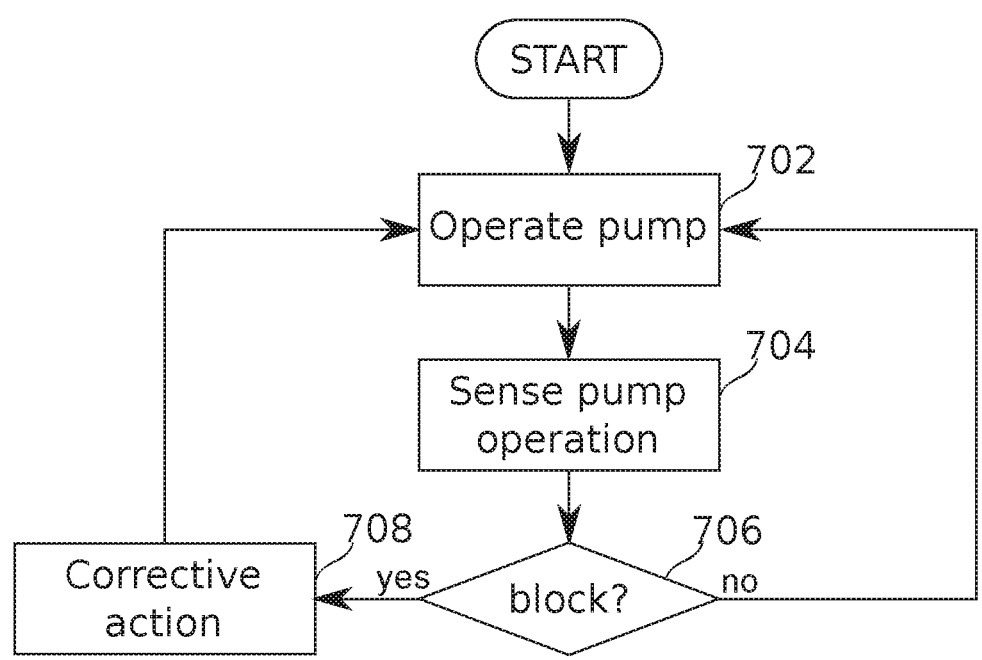
FIG. 7 is a flowchart schematically outlining a method of using sensed pump operation to detect blockage, according to some embodiments of the present invention.

Reference is now made to FIG. 7, which is a flowchart schematically outlining a method of using sensed pump operation to detect blockage, according to some embodiments of the present invention. At block 702, a pressure source 108 comprising a pump (optionally, a positive displacement pump) is operated. At block 704, operation of the pump is sensed, for example, using sensor 108A.

At block 706, in some embodiments, a determination is made if the characteristics of the sensed pump operation indicate a potential blockage of an evacuation lumen. In some embodiments of the invention, changes comprising slowed pumping/increased power meeting one or more criteria are interpreted as indicating evacuation lumen blockage. Optionally, the criteria comprise exceeding a threshold (e.g., of slowed speed and/or increased power consumption). Optionally, the threshold is adjusted based on operating conditions such as current estimated liquid/gas evacuation ratio.

Optionally, if blockage is sensed, corrective action is taken at block 708. In some embodiments, the corrective action comprises controller 130 reducing an estimate of evacuated material volume. Optionally, this reduced estimate affects the delivery of replacement insufflation gas and/or irrigation fluid. In some embodiments, sensed blockage is a trigger for actions to purge the blockage. For example, the controller 130 slows and/or stops the pump (e.g., to release tissue which may be blocking an intake aperture of the evacuation lumen). Optionally, controller 130 reverses the pump direction and/or switches in a source of positive pressure (e.g., to try to dislodge an intralumenal block).

Figure 2:
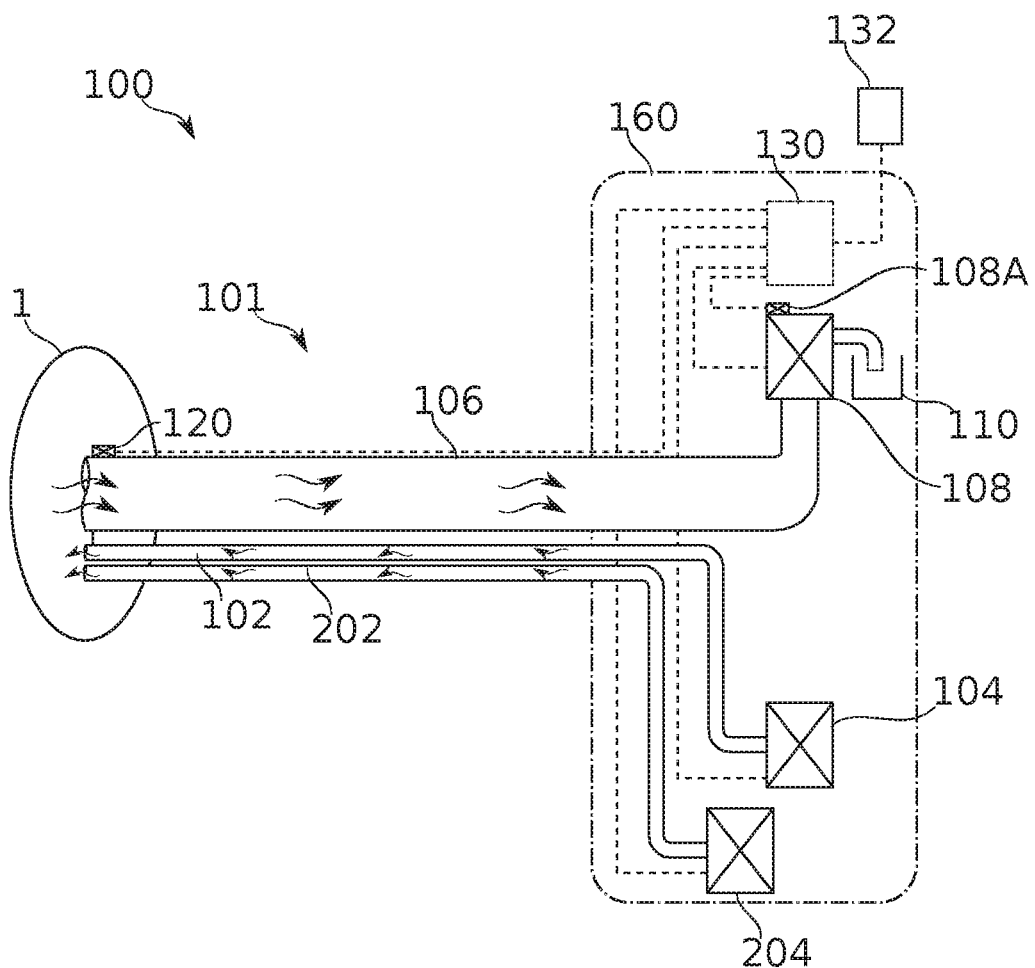
FIG. 2 is a schematic drawing of a colon cleansing system comprising insufflating apparatus for automatic maintenance of a non-collapsed colon state and a separate irrigating subsystem, according to some exemplary embodiments of the invention.

Continuing descriptions with respect to FIGS. 1A-1B and 2: in some embodiments of the invention, an operator-activated control 132 (for example, a foot pedal) is provided. Operator control 132 is optionally used to activate evacuation, irrigation and/or insufflation, the details of which are managed through controller 130. Optionally, further control is provided with control 132, for example to allow independent activation of various matter flux conduits, and/or to allow finer-grained control of the supply amounts and/or periods.

A typical use configuration of a colon cleaning device 100 is together with a colonoscope comprising a colonoscope probe 150 and associated optical box 152. In some embodiments of the invention, a colonoscope probe 150 and cleaning probe 101 are provided as an integral unit. In some embodiments, cleaning probe 101 comprises a disposable section 170. In some embodiments, disposable section 170 is attached to and/or over colonoscope probe 150 at or about the time of use, and inserted to a colon therewith.

Monitoring and Control of Insufflation

Pressure at the distal end 101A of the cleaning probe 101 provides a convenient parameter for feedback-controlled maintenance of a non-collapsed colon state. In some embodiments, the controller acts to maintain a selected pressure range within the colon, for example, the 5-40 mbar range. In some embodiments, the range of pressures targeted is another pressure range, for example, 5-10 mbar, 5-20 mbar, 3-25 mbar, 10-30 mbar, 7-40 mbar, or another pressure range having the same, higher, lower, and/or intermediate bounds. In some embodiments, only a minimum pressure of a range is actively regulated. In some embodiments, the targeted range of pressures is variable. Optionally, variability of a targeted pressure range is on the basis of, for example, independently observed inflation state, reported discomfort, a need for transitory increases to transit a particular constriction, or another reason.

In some embodiments, more than one target range exists simultaneously, multiple upper and/or lower limits are described, and/or the selection of currently active insufflation/irrigation/evacuation parameters is a variable function of measured pressure. In some embodiments, different pressures are associated with different actions activated by the controller 130; for example, a greater or lesser aggressiveness in supplying/removing material to move away from and/or toward a limit.

With respect to preventing collapse, for example, a first lower limit (5 mbar, for example) is set in some embodiments as a hard limit, to avoid underinflation and consequent collapse. Actions to stay above this limit include, in some embodiments, increasing supply of insufflating gas, and/or action affecting other activities of the cleaning system, such as temporary cessation of evacuation and/or increase of irrigation supply. In some embodiments, a second limit (20 mbar, for example) is set as a soft target limit, above which automatic insufflation stops, and below which insufflation is initiated (but the limit is not in itself a limit which must not be crossed over; for example, insufflation starts or stops after a delay, after a further change in pressure, and/or according to another further criterion). It is a potential advantage to provide a soft target limit, to provide a target pressure which is safely away from limits of danger and/or collapse. In some embodiments, a particular target pressure limit is replaced by a range limit once reached, and insufflation or another corrective action starts not when the target pressure is left, but when the newer (and wider) range limit is left. Potentially, this avoids continuous operation and/or operation cycling of an insufflation subsystem, reducing interference with other activities. Optionally, a rate of insufflation increases (in one or more steps, and/or continuously) between a soft limit and a hard limit or another soft limit, potentially assisting in avoidance of reaching a near-collapse or overinflation situation.

With respect to preventing overinflation, in some embodiments, a hard upper pressure limit is set (for example, 40 mbar) above which aggressive action is commanded by controller 130 to prevent potential damage due to overinflation. For example, insufflation is prevented, evacuation is turned on, and/or irrigation is prevented. In some embodiments, an overpressure vent and/or valve is provided, for example a vent in an insufflation conduit 102, whereby a potentially dangerous level of pressure is vented to the outside (for example, at base station 160 or at some other point external to the colon). Optionally, sensed overpressure activates a mechanism to equalize pressure within the colon, for example, by opening a vent along the length of insufflation conduit 102 within the colon.

It is, however, a potential advantage to avoid venting back through an insufflation conduit, to avoid contamination with waste which could render it inoperable. It is a potential advantage to avoid approaching a pressure limit requiring full or partial system shutdown. In some embodiments, an at least second upper range limit is set (for example 30 mbar) above which controller 130 operates pressure sources 108, 104, 204 under its control to bias the net flow of mass toward reduction of volume and/or pressure within the colon. For example, evacuation operations are extended and/or increased in rate of volume extracted. Also for example, a rate of compensating insufflation accompanying evacuation is reduced, optionally to the point of stopping insufflation altogether. In some embodiments of the invention, a command to provide extra insufflation (for example, to assist in transiting a difficult constriction) is ignored and/or reduced in effect above some range limit. It is to be understood that controllable actions subject to graded responses (such as rates of flow) are optionally modulated by controller 130 in some embodiments as substantially continuous functions of colon inflation state.

Additional or Alternative Inflation State Monitoring and/or Control

A pressure sensor 120 comprises a convenient device for measuring colon inflation state, but it is to be understood that any measurement device which indicates colon inflation state provides a potential source of input to controller 130. For example, controller 130, in some embodiments, tracks the volume of material introduced to and/or removed from the colon, relating it to the known and/or expected volume capacity of a colon. This can be performed, for example, by use of volume-calibrated pressure sources. Although this method of inflation state tracking is subject to error (for example, the colon capacity itself is difficult to estimate, volume is not necessarily distributed evenly through the colon, and/or it is difficult to track volumes which leak from the anus), it can be used alone for providing an approximation of colon state, or, with potentially greater safety, provide a useful check on another measurement, such as a pressure measurement. In some embodiments, an expected change in pressure is calculated by controller 130 based on the volume commanded and/or measured to be introduced and/or removed.

In some embodiments, the relationship between expected and measured changes in pressure allows closer tracking of the effects of insufflation on colon inflation state. For example, an unanticipated drop in pressure potentially indicates leakage from the colon, and/or among compartments of the bowel, for example, due to the sudden opening of a constriction and/or blockage. Additionally or alternatively, an unanticipated rise and/or fall in pressure potentially indicates peristaltic contraction and/or another movement such as shifting of the orientation of the subject. In some embodiments of the invention, changes in pressure which relate to one of these or another event not commanded by the controller are treated differently than commanded pressure changes. For example, in some embodiments, the magnitude of a non-commanded rise in pressure is a basis for setting the magnitude (in mbar, for example) of a pressure safety buffer needed to avoid exceeding a safety limit. For example, if a 40 mbar pressure is to be avoided, observation of a 10 mbar excursion in pressure indicates, in some embodiments, that normal operating pressure should be maintained below 30 mbar. In some embodiments, non-commanded pressure changes are taken as an indication of uncertainty of the current colon inflation state. For example, a target minimum pressure of 5 mbar is considered to be reached, in some embodiments, if an uncertainty of pressure measurement is about 2 mbar, and a measured pressure of 7 mbar is observed. Optionally, operations affecting insufflation are suspended or reduced in magnitude until pressure state stabilizes after a non-commanded excursion. In some embodiments, a drastic and/or sustained mismatch in the pressure-volume relationship is reported as evidence of a potential malfunction, for example, by activation of an alarm state in the system.

In some embodiments, another sensing means for indicating colon inflation state is provided. For example, an indication of colon diameter in the vicinity of the distal end 101A of the colon cleaning device is potentially provided by a camera view of a colonoscopy device (suitably processed), and/or by acoustic monitoring (for example, by ultrasound).

In some embodiments of the invention, a human operator directly and/or indirectly provides input which affects the insufflation state. In some embodiments, for example, a control means 132 comprises a foot pedal, which signals a command to initiate evacuation when pressed. Insufflation is optionally commanded by controller 130 as a side effect of this, in order to maintain an appropriate colon inflation state. In some embodiments, another control is provided (for example, a second foot pedal and/or another switch) which allows a directly commanded increase in insufflation, for example, to assist in the passage of an obstruction, such as a constriction between two segments of the colon. Optionally, a control for manually slowing or stopping insufflation is provided, for example, to allow evacuation without or with reduced insufflation volume.

In some embodiments of the invention, parameters used for automatic maintenance of insufflation are manually adjustable, at least in part. Optionally, a lower insufflation pressure limit can be raised by an operator, for example to overcome conditions when colon collapse is occurring at a higher than usual pressure. This is a potential consequence when shifting a patient is found to change the pressure of weight of other internal organs on the colon such that it is more prone to collapse than usual. Also optionally, an upper insufflation pressure limit can be lowered, for example to reduce a level of discomfort for a subject undergoing a procedure. Such adjustment is, for example, to a specific pressure limit, and/or to another parameter such as a rate of insufflation, a relationship of insufflation rate to pressure, and/or another parameter affecting insufflation and/or insufflation relative to other functions of the cleaning system such as evacuation and/or irrigation.

Exemplary Inflation

Figure 3:
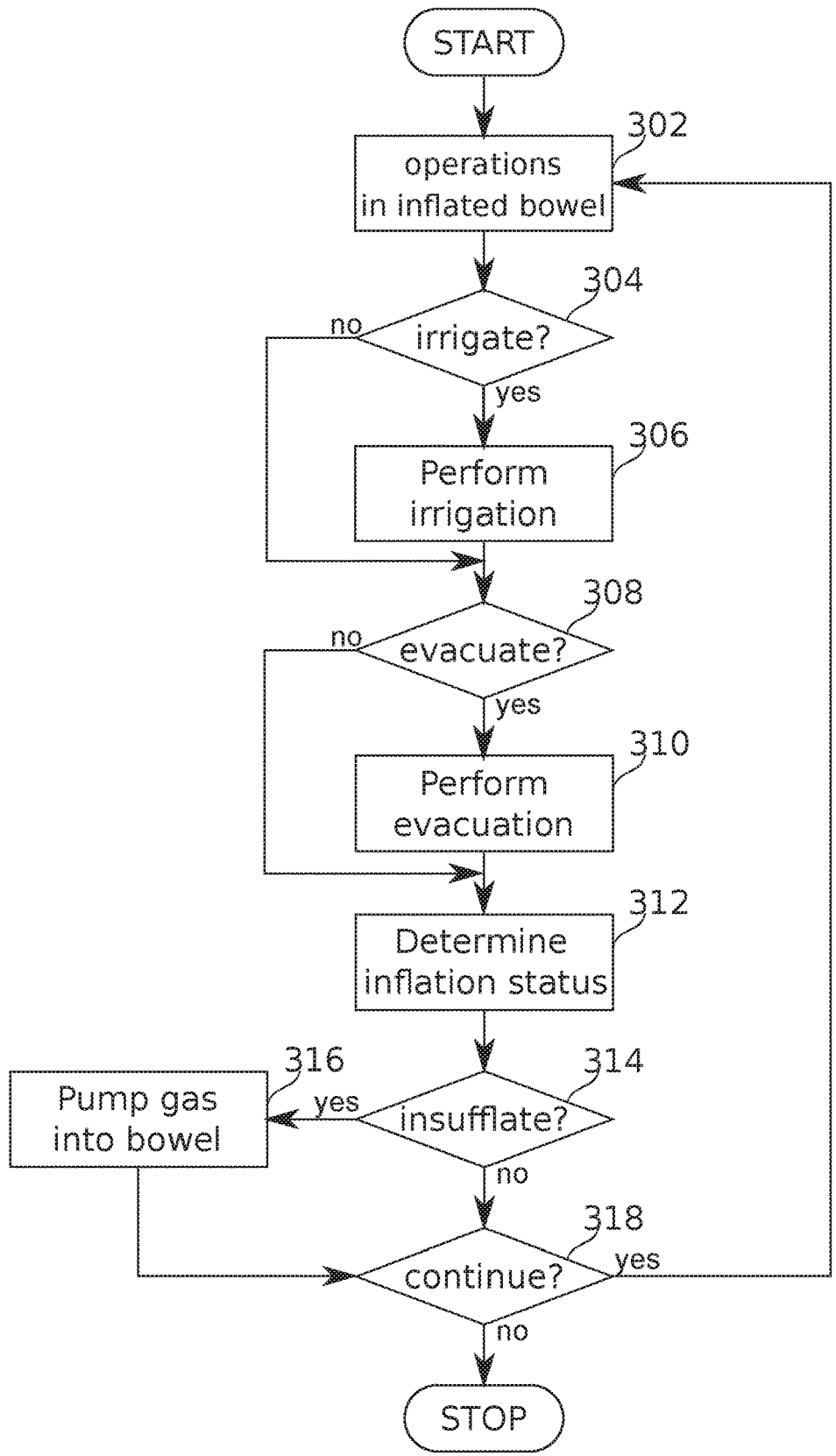
FIG. 3 is a schematic flow chart of colon inflation maintenance during cleansing and/or inspection of a colon, according to some exemplary embodiments of the invention.

Reference is now made to FIG. 3, which is a schematic flow chart of colon inflation maintenance during cleansing and/or inspection of a colon, according to some exemplary embodiments of the invention.

In some embodiments of the invention, a method is provided which for automatically obtaining and/or maintaining a target inflation state of a colon. Optionally, the method is performed in parallel with colon cleaning operations such as irrigation and/or evacuation, which potentially interfere with preserving a proper bowel inflation state.

It is to be understood that the operations of the blocks of FIG. 3, while described sequentially for purposes of exposition, are optionally performed simultaneously, and/or in any reasonable order supported by the colon cleaning system used. For example, irrigation, evacuation, and insufflation are optionally performed simultaneously, and/or in any relative respective order. Likewise, decision blocks, insofar as they are decidable independent of other action and/or decision blocks, are optionally resolved simultaneously and/or in any reasonable order.

At block 302, in some embodiments, operations involving an apparatus comprising a colon cleaning system are underway in an inflated bowel. Optionally, the colon cleaning system is, for example, a system such as is shown in and/or described in relation to FIGS. 1A-2. Optionally, the apparatus comprises a colonoscope. In some embodiments, the operations being performed include operations typical of a colonoscopy procedure, for example, manipulating a colonoscope to advance it to the distal end of a colon, and/or withdrawing the colonoscope. Optionally operations comprise inspecting the colon for lesions.

At block 304, in some embodiments, a determination is made to irrigate the colon, or not. Irrigation, in some embodiments, is decided for based upon a need to break apart, loosen, suspend, and/or dissolve waste encountered in the colon during colonoscopy operations. The flowchart skips to block 308 if irrigation is not to be performed, and continues with block 306 otherwise.

At block 306, in some embodiments, irrigation is performed. Irrigation, in some embodiments, comprises introducing fluid to the colon from a probe 101 comprising an irrigating conduit 202 of a colon cleaning device, and/or from a probe 150 of a colonoscope. The fluid comprises, for example, liquid, gas, or both. In some embodiments, irrigation comprises a flowing introduction of a liquid such as water or saline to the colon. In some embodiments, irrigation comprises a jetting action imparted by a nozzle constriction. Optionally, jets are actively and/or passively directed to impart mechanical energy to fecal matter encountered in the colon, potentially assisting in breaking it apart.

At block 308, in some embodiments, a determination is made to evacuate material from the colon, or not. Evacuation, in some embodiments, is decided for based upon the presence of irrigation fluid and/or fecal matter in the vicinity of the bowel near the distal end of the cleaning apparatus probe. In some embodiments, a determination to irrigate and to evacuate comprises a single determination that there is fecal matter which there is a need to remove from the colon. In some embodiments, evacuation and/or irrigation are triggered by a command from an operator, for example by pressing on a foot pedal or other operator control 132. The flowchart skips to block 312 if evacuation is not to be performed, and continues with block 310 otherwise At block 310, in some embodiments, evacuation is performed. In some embodiments of the invention, evacuation comprises activation of an evacuation pressure source 108 coupled to an evacuation conduit 106. In some embodiments, evacuation itself is an automatically monitored and managed sequence of events, wherein exceptions such as blockage are detected (for example, by pressure changes observed), and dealt with, for example by adjustments to the pressure applied to evacuation conduit 106. Potentially, evacuation alternates between removal of—primarily—irrigation fluid and/or waste suspended therein, and removal of—primarily—gas inflating the colon. Alternation is, for example, a result of movement of an intake aperture of the evacuation conduit in the colon and/or of changing levels of liquid and suspended material to be evacuated. In some embodiments of the invention, volume removed per unit of time varies as a function of automatically commanded changes in evacuation rate (for example, to purge blockages), and/or as a function of the mass and/or viscosity of the material (gas, fluid and/or solid) being evacuated. In some embodiments, variable rate of evacuation is measured by measurement of evacuated volume.

At block 312, in some embodiments, inflation status of the colon is determined. In some embodiments, determination comprises measurement of a pressure at one or more sensors 120. In some embodiments, determination of inflation status comprises relating sensed pressure to volumetric measurements of material input/outtake from the colon. In some embodiments, determination of inflation status comprises another input, such as a determination of inflated colon diameter.

At block 314, in some embodiments, a determination is made to insufflate a colon, or not. Optionally, the determination is made based on the inflation status of the colon determined at block 312. In some embodiments wherein inflation status is determined based on a measured pressure, a determination to insufflate comprises comparing the measured pressure against one or more target pressures, the insufflation determination comprising choosing an action based on predetermined actions for a range within which the currently measured pressure falls. For example, insufflation is provided at or below 10 mbar, or at or below another target pressure, for example, 5 mbar, 7 mbar, 9 mbar, 12 mbar, 15 mbar, 20 mbar, or another higher, lower, or intermediate pressure. In some embodiments, insufflation supply tapers off as a target pressure is approached, such that a very low pressure (such as a pressure below 5 mbar) results in a maximum inflation rate, while a pressure close to a target inflation pressure results in a relatively slow inflation rate; for example, a maintenance rate of inflation chosen to counteract leakage, or no inflation.

In some embodiments, determination to add (or not) inflating gas comprises filtering a current pressure reading based on additional information such as recent sampling history, expected pressure based on volume adding and/or removal activity, or another additional input.

Optionally, a baseline volume of insufflation is selected to equal or approximate a commanded volume of material evacuation, optionally reduced by a volume of supplied irrigation fluid. Measurement of actual pressure change is optionally used as an error correcting signal for the baseline volume.

In some embodiments, there is potentially a partial disconnection in the providing of insufflation and/or suction between sensing of a pressure change and supply of the correction. For example, supply itself is potentially subject to lags, for example, due to pump starting times and/or fluid capacitance in supply lines. Additionally or alternatively, the supply and/or suction capacity is potentially limited (for example, conduit inner diameter and/or a maximum pressure differential are limited relative to need). Optionally, a first fluid conduit (for example for supply of insufflation gas) is operated at a relatively constant rate (for example, to reduce shaking and/or discomfort), while a second fluid conduit (for example, for supply irrigation fluid or suction) is operated at need for the operations of cleaning and/or purging. Such configurations are optionally met by setting a target pressure range wide enough to allow partially asynchronous supply of fluids and/or pressures.

Optionally, a target pressure range and/or supply/removal balance is adjusted, for example, to allow smoothing out a rate of fluid and/or suction delivery, and/or in anticipation of a future situation. For example, rather than maintaining colon pressure in the middle of a safe range, the colon pressure and/or target colon pressure is elevated beyond that pressure by a few mbar (1-10 mbar, for example), in anticipation of more suction being applied and/or leakage occurring. For example, after operation of an irrigation channel, it is potentially anticipated that a period of increased suction will occur (for example, in order to clear the irrigation fluid). Optionally, a basal rate of insufflation immediately rises (with or without a pressure drop to trigger it), for example, to allow providing a smoother flow of insufflation gas during the period of suction (potentially avoiding a need for repeated starts and stops by building in a pressure buffer). Optionally, a change in a rate of pressure leakage is detected, and extrapolated to a future rate of leakage (for example, by a linear extrapolation). Optionally, insufflation gas is adjusted beyond current requirements for pressure maintenance, in anticipation of a higher future requirement for adjustment.

Optionally, a lower pressure target is set before, upon, and/or during a commanded supply (for example, of irrigation fluid), potentially allowing a larger reserve of pressure range to buffer a general tendency for pressure to increase.

Figure 5:
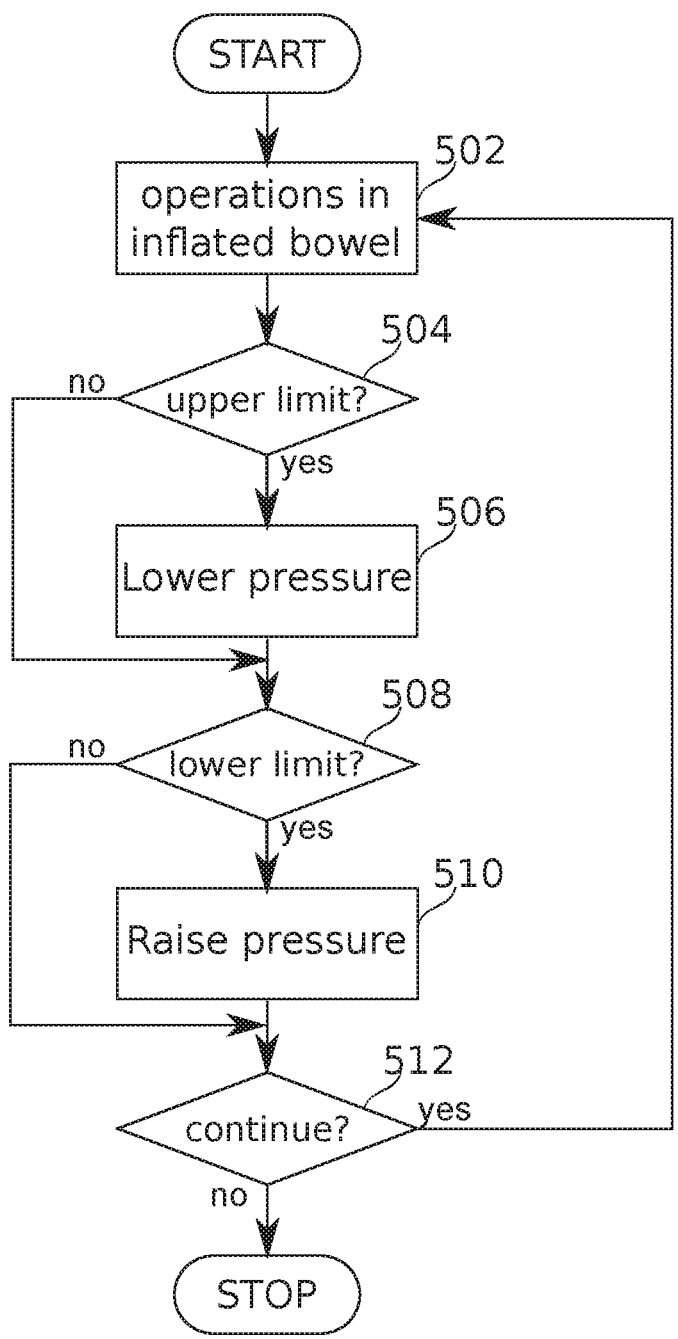
FIG. 5 is a schematic flowchart of the maintenance of colon inflation state during cleansing and/or inspection of a colon, according to some exemplary embodiments of the invention.
Figure 6:
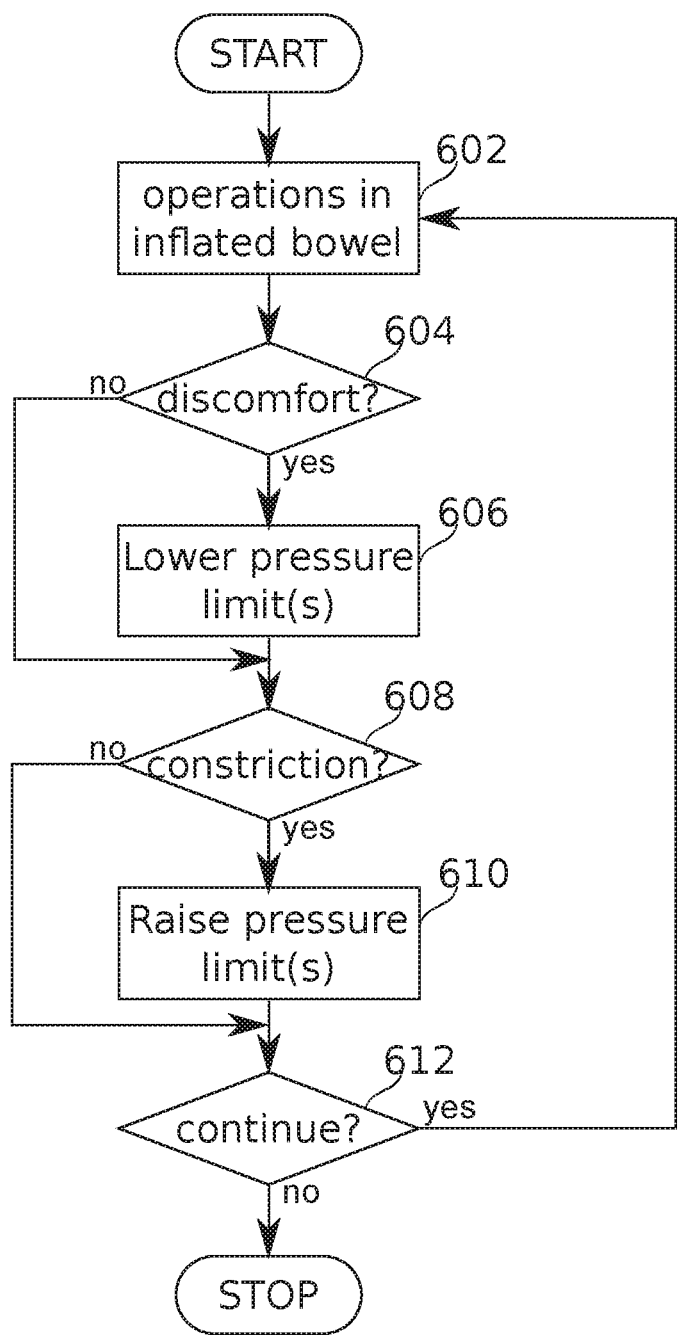
FIG. 6 is a schematic flowchart of selection and/or modification of a target colon pressure range during cleansing and/or inspection of a colon, according to some exemplary embodiments of the invention.

FIGS. 5 and 6 describe features of embodiments where the determination of an action related to inflation state comprises further considerations, including active reduction of insufflation pressure and/or modification of an inflation state target range.

In some embodiments, an operator command is a triggering event for insufflation.

If inflation is to occur, the flowchart continues at block 316. Otherwise, the flowchart branches to block 318.

At block 316, in some embodiments, gas is pumped into the bowel, according to the determination made at block 314. Optionally, the rate of gas inflow is, for example, 10-100 ml/min, 30-200 ml/min, 50-1000 ml/min, or another range of flow rates having the same, intermediate, higher and/or lower bounds. Optionally, a period during which inflation occurs before another determination is preset to be from a few milliseconds to a few seconds (for example, 10 milliseconds, 10 seconds, or another greater, smaller, or intermediate period). In some embodiments, rate of inflation is a function of distance from a target pressure or pressure range. For example, a relatively high rate is provided when colon inflation state is near a collapse point, a lower rate (optionally, a gradually and/or step-wise decreasing rate) for higher pressures, and no inflation is provided if a target for pressure has been reached.

At block 318, in some embodiments, if operations in the inflated bowel are to continue, the flowchart returns to block 302. Otherwise, the flowchart ends.

Figure 4:
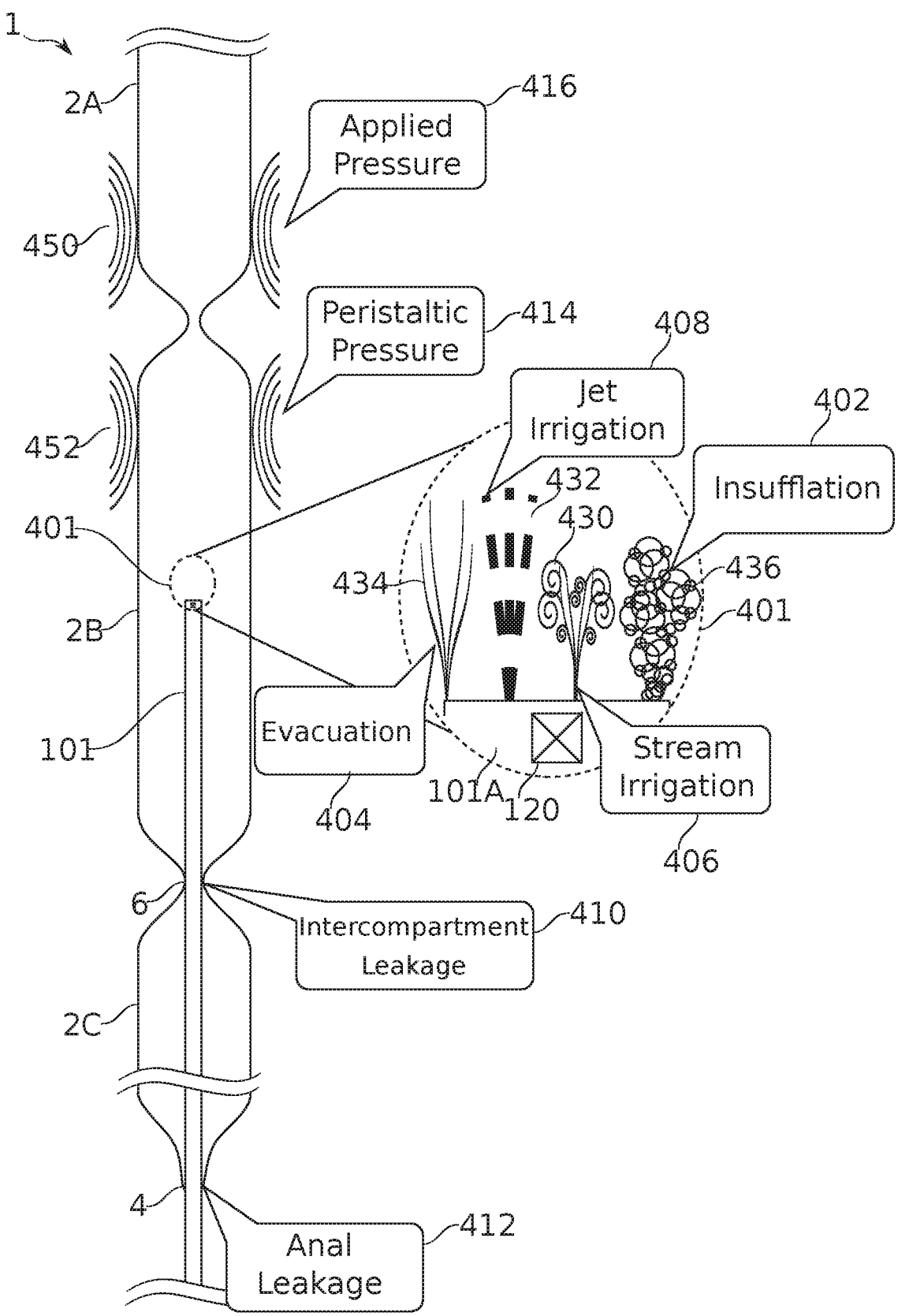
FIG. 4 is a schematic diagram of potential sources of change in colon inflation state during cleansing and/or inspection of a colon, according to some exemplary embodiments of the invention.

Reference is now made to FIG. 4, which is a schematic diagram of potential sources of change in colon inflation state during cleansing and/or inspection of a colon, according to some exemplary embodiments of the invention.

In an idealized scenario for preventing colon collapse during colon cleaning, the inflation state of a colon 1 can be considered as a single inflated chamber 2B, which a pressure measurement device 120 located on the distal end 101A of a probe 101 samples. Changes to this inflation state are made by introducing and/or removing material from a region 401 around the distal end 101A of a cleaning system probe 101. For example, evacuation 404 reduces pressure in the colon by removing volume of fluid, solid, and/or gas 434. Irrigation, optionally jetting 408 or streaming 406, adds volumes of fluid and/or gas 432, 430. The balance of pressure required to maintain inflation is provided as necessary by insufflation 402 of gas 436.

In some embodiments, consideration for additional factors affecting colon inflation state is taken. For example, a colon is potentially divided into two or more separate pressure compartments 2A, 2B, 2C, due to closed or relatively closed restrictions 6 along the length of the intestine. Since sensor 120, in general, senses the same compartment as that to and from which material is moved, it is sufficient, in some embodiments, to ignore the status of other compartments. However, other compartments potentially act as sinks and/or stores for pressure, allowing changes in pressure to occur due to intercompartment leakage 410. Anal leakage 412 can also occur due to material leaking from the anus 4. In some embodiments, tracking of colon inflation state comprises relating net changes in the volume of introduced material to the colon to colon pressure. Potentially, this allows anticipation of pressure changes to preserve a more constant inflation state. For example, a sudden decrease in pressure relative to expectations implies a leak. In some embodiments, a rate of insufflation is increased to quickly counteract the leak, even though the pressure itself remains at a sufficiently high level that inflation is not yet necessary based on a pure input/output model of colon pressure.

In some embodiments, consideration is taken for pressure-increasing events apart from the flux of matter through the cleaning system. These include, for example, applied pressure 416, such as that due to the shifting weight of internal organs on the colon 450, and/or peristaltic pressure 414, caused by muscular contractions 452 of the colon itself. In some embodiments of the invention, a controller 130 is configured to treat an increase in pressure which is unaccounted for by mass flux through the cleaning system as a transient to be disregarded, rather than take action to correct for it. Nevertheless, additionally or alternatively, the size of transients is optionally noted, and a safety margin built in to the currently maintained target pressure, such that an uncomfortable and/or dangerous pressure is unlikely to be reached due to repeated such transients.

Reference is now made to FIG. 5, which is a schematic flowchart of the maintenance of colon inflation state during cleansing and/or inspection of a colon, according to some exemplary embodiments of the invention.

It is to be understood that the operations of the blocks of FIG. 5 (and/or, for example, FIG. 6), are optionally performed simultaneously, and/or in any reasonable order supported by the colon cleaning system used. Adjustment of pressure, in particular, optionally occurs simultaneously with ongoing operations comprising use of a colon cleaning system in a bowel. Likewise, decision blocks, insofar as they are decidable independent of other action and/or decision blocks, are optionally resolved simultaneously and/or in any reasonable order.

At block 502, in some embodiments, operations using an apparatus comprising a colon cleaning system are underway in an inflated bowel are underway. Operations and/or a colon cleaning system apparatus used are, for example, as described in relation to FIG. 3, hereinabove.

At block 504, in some embodiments, a determination is made by controller 130 as to whether or not an upper pressure limit is exceeded. Pressure limits of different types are described, for example, in relation to the section Monitoring and Control of Insufflation, hereinabove. In some embodiments, an upper limit is a hard limit, above which pressure must not go due to reasons of safety or minimum patient comfort. An additional or alternative upper limit is a soft limit, which marks an upper bound of a targeted pressure range below a safety limit. Excursions of pressure above a soft limit are optionally permitted, for example, by deliberate command from an operator for a temporary opening of a constricted region, and/or due to a pressure transient, for example due to shifting weight and/or peristaltic motions, as described in relation to FIG. 4 hereinabove. In some embodiments, more than one soft upper limit is defined, for example, in relation to pressure elevations having different causes. In some embodiments, a pressure limit is defined as switching point—above and below it, different actions are performed until the limit is again reached. In some embodiments, a limit is defined as a point from or toward which an action is gradually begun as pressure changes, the rate of approach to full activity or full stoppage being set to occur at the limit point itself. Such an action is, for example, a rate at which insufflation, irrigation, and/or irrigation occurs.

If an upper pressure limit is exceeded, in some embodiments, the flowchart continues at block 506. Otherwise, the flowchart continues at block 508.

Additionally or alternatively, another measurement providing a metric which describes a state of colon inflation is optionally used by controller 130 as a basis for determining that action should be taken. Such measurements are described, for example, in the section Additional or Alternative Inflation State Monitoring and/or Control, hereinabove.

At block 506, in some embodiments, controller 130 issues one or more commands which change the operation of the colon cleaning device 100 such that a colon inflation state is decreased. In some embodiments (and depending on the definition of the limit, as for other possible actions), ongoing insufflation is halted. In some embodiments, for example, if a safety-critical limit is exceeded and/or in danger of near approach, evacuation is started (whether or not commanded by an operator) in order to reduce colon pressure proactively. In some embodiments, for example, as a less critical high limit is gradually approached and/or exceeded, the rate of evacuation, when it is commanded, is correspondingly raised. Potentially, this allows a target pressure range to be actively restored more quickly. In some embodiments, the rate of evacuation is raised, for example, by 10%, 20%, 30%, 50%, or by another larger, smaller, or intermediate relative amount. In some embodiments, a commanded evacuation lasts for a period longer than otherwise executed in response to the command, the extension of the period being for example, by 100 msec, 500 msec, 1 sec, 2 sec, 5 sec, or another longer, shorter or intermediate period. In some embodiments, the activation of insufflation together with evacuation is reduced and/or stopped for as long as measured pressure is in a particular range above some predetermined limit. In some embodiments, irrigation volume is reduced, for example by reducing the amount of gas provided along with liquid, and/or by reducing the overall pressure at which irrigation fluid is provided.

At block 508, in some embodiments, a determination is made as to whether or not measured pressure is less than a lower limit of pressure. In this case, a "hard" lower limit is set, for example, at a limit below which collapse of the colon is probable. One or more soft limits (defined as pressure ranges and/or particular pressures) are potentially set, and associated with a remedying action, propensity, and/or intensity thereof.

If a lower pressure limit is undershot, in some embodiments, the flowchart continues at block 510. Otherwise, the flowchart continues at block 512.

At block 510, in some embodiments, action is commanded by controller 130 to raise the inflation pressure of the colon. Action to increase pressure, in some embodiments, includes, for example, sending and/or modifying commands to an insufflation pressure supply 104. Optionally, this comprises starting insufflation (particularly if a hard limit has been reached), increasing a rate of insufflation, and/or increasing a rate at which insufflation occurs when it is otherwise activated (for example, if activated together with an evacuation command). The increase of insufflation rate is, for example, 10% of a default rate, or 30%, 50%, or another larger, smaller or intermediate relative rate. Similarly to the extension of evacuation time in the high-limit case, insufflation which is, in some embodiments, triggered along with evacuation is optionally extended by a period according to a pressure limit and/or distance therefrom by, for example, 100 msec, 500 msec, 1 second, 2 seconds, 5 seconds, or another longer, shorter, or intermediate period. In some embodiments, increases of rate and/or extension of time are applied additionally or alternatively to operation of an irrigation supply 204. In some embodiments, if a limit of a rate of insufflation and/or irrigation is reached, evacuation intensity is reduced (by so-commanding an evacuation pressure supply 108), the reduction being, for example, by 10%, 30%, 50%, or another larger, smaller, or intermediate relative amount.

At block 512, in some embodiments, if operations in the inflated bowel are to continue, the flowchart returns to block 502. Otherwise, the flowchart ends.

Reference is now made to FIG. 6, which is a schematic flowchart of selection and/or modification of a target colon pressure range during cleansing and/or inspection of a colon, according to some exemplary embodiments of the invention.

At block 602, in some embodiments, operations using an apparatus comprising a colon cleaning system 100 are underway in an inflated bowel are underway. Operations and/or a colon cleaning system apparatus used are, for example, as described in relation to FIG. 3, hereinabove.

At block 604, in some embodiments, a determination is made if there is a reason to lower a pressure limit currently used by the colon cleaning system 100. In particular, discomfort reported by the subject is a basis for lowering the pressure limit. A lowered limit optionally comprises a hard limit and/or a soft limit, for example, as described in relation to FIG. 5 hereinabove. Even if no discomfort is reported, a cleaning system operator optionally sets a reduced pressure limit, based, for example, on previous experience, or a perceived lack of an overriding reason for a higher pressure limit to prevent colon collapse. For example, when leakage, peristalsis, and/or internal organ pressure appears unlikely to increase a danger of collapsing the colon during the procedure, an operator optionally elects to reduce a target pressure such that the pressure within the colon is generally reduced during the ongoing procedure.

If a pressure limit is indicated, in some embodiments, the flowchart continues at block 606. Otherwise, the flowchart continues at block 608.

At block 606, in some embodiments, a pressure limit used in control determinations by a controller 130 is lowered. In some embodiments, a limit is lowered, for example, by 1-5 mbar, 4-8 mbar, 5-10 mbar, 8-15 mbar, or by a pressure in another range having the same, lesser, greater, and/or intermediate bounds. In some embodiments, the particular amount of lowering is selected by an operator. In some embodiments, the amount of lowering is determined by shifting to a different predetermined preset group of pressure limits describing parameters used in control determinations by controller 130.

At block 608, in some embodiments, a determination is made that there is a reason to increase a pressure limit. The reason for increase is, for example, due to encountering a constriction in the bowel which may be opened by an increase in the insufflation pressure. Additionally or alternatively, an operator notes an increased risk for bowel collapse, for example due to leakage, peristalsis, and/or weight on the colon section being traversed. In some embodiments, the determination is for a persistent rise in pressure. In some embodiments, the determination is for a transient rise; for example, a rise that lasts long enough to cross a difficult region of constriction.

If a pressure limit is indicated, in some embodiments, the flowchart continues at block 610. Otherwise, the flowchart continues at block 612.

At block 610, in some embodiments, a pressure limit used in control determinations by a controller 130 is raised. In some embodiments, a limit is raised, for example, by 1-5 mbar, 4-8 mbar, 5-10 mbar, 8-15 mbar, or by a pressure in another range having the same, lesser, greater, and/or intermediate bounds. In some embodiments, the particular amount of raising is selected by an operator. Additionally or alternatively, the amount raised is determined by shifting to a different preset group of control parameters.

At block 612, in some embodiments, if operations in the inflated bowel are to continue, the flowchart returns to block 602. Otherwise, the flowchart ends.

It is expected that during the life of a patent maturing from this application many relevant controllers will be developed and the scope of the term controller is intended to include all such new technologies a priori.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A colon cleaning system for evacuating material from a distal end of a colon while keeping the colon in a safely inflated state allowing internal observation, the colon cleaning system comprising:
    an evacuation conduit having a distal region insertable to the colon to communicate suction for evacuating the material;
    an irrigating subsystem comprising an irrigation conduit, and an irrigation source configured to supply an irrigating fluid comprising liquid through the irrigation conduit to the colon;
    an insufflation subsystem comprising a gas source, and an insufflation conduit configured to supply insufflation gas without liquid from the gas source to inflate the colon;
    wherein said irrigation conduit and said insufflation conduit are separate from one another;
    a controller; and
    a pressure sensor configured to provide pressure measurements from the distal region to the controller;
    wherein the controller is configured to regulate a flow of the supply of insufflation gas and the suction to produce and maintain the safely inflated state, based on the pressure measurements, including regulation that supplies the insufflation gas through the insufflation conduit while restricting flow of the irrigating fluid from the irrigation source; and
    wherein said evacuation conduit, said irrigation conduit, and said insufflation conduit are introducible into the colon; and
    wherein a colonoscope is configured to be introduced into the colon external to the insufflation conduit.

2. The colon cleaning system of claim 1, wherein the system comprises a sensor configured to measure a relative proportion of gas in an evacuated mixture of at least gas and liquid evacuated through the evacuation conduit; and wherein the controller is also configured to adjust the supply of insufflation gas, based on the relative proportion of gas in the evacuated mixture of at least gas and liquid.

3. The colon cleaning system of claim 1, wherein the distal region comprises a connector which attaches to the colonoscope for insertion to the distal end of the colon.

4. The colon cleaning system of claim 1, wherein the controller is configured to regulate the flow of the supply of insufflation gas and the suction to keep the pressure measurements from the pressure sensor within a predetermined range of pressures consistent with the safely inflated state allowing internal observation.

5. The colon cleaning system of claim 4, wherein the predetermined range of pressures comprises upper and lower bounds both between 5 mbar and 40 mbar above ambient pressure.

6. The colon cleaning system of claim 1, wherein the supply of insufflation gas is increased based on a decreasing value of the pressure measurements.

7. The colon cleaning system of claim 1 wherein the supply of insufflation gas is variable by the controller to multiple different supply rates and/or pressures as the pressure measurements change.

8. The colon cleaning system of claim 1, wherein flow regulation by the controller to maintain the safely inflated state also includes regulation that supplies the irrigating fluid from the irrigation source to the irrigation conduit while also supplying the insufflation gas through the insufflation subsystem.

9. The colon cleaning system of claim 8, wherein the controller is configured to reduce the supply of insufflation gas as a function of an increase in the supply of irrigating fluid.

10. The colon cleaning system of claim 1, wherein the evacuation conduit is attached to a positive displacement pump providing the suction for evacuating the material.

11. The colon cleaning system of claim 10, wherein the controller is configured to maintain the safely inflated state of the colon, based on an estimated volume of the material removed by the suction from the colon by the positive displacement pump.

12. The colon cleaning system of claim 11, wherein the estimated volume is based on a speed of operation of the positive displacement pump.

13. The colon cleaning system of claim 11, wherein the estimated volume is based on power consumption by the positive displacement pump.

14. The colon cleaning system of claim 1, wherein said irrigating subsystem and said insufflation subsystem are separate from one another.

15. The colon cleaning system of claim 1, wherein said pressure sensor is attached to an outer surface of said evacuation conduit.

16. The colon cleaning system of claim 1, wherein said colonoscope is external to said evacuation conduit, said irrigation conduit, and said insufflation conduit.

17. The colon cleaning system of claim 1, wherein said colonoscope is configured to extend side by side, along the length of said evacuation conduit, said irrigation conduit, and said insufflation conduit.

18. The colon cleaning system of claim 1, wherein said system includes a portion insertable into the colon, said insertable portion configured to be positioned relative to the colonoscope such that the colonoscope is at an external location relative to said insertable portion.

19. The colon cleaning system of claim 1, wherein said colonoscope is configured to be introduced into the colon external to and adjacent to the evacuation conduit, the irrigation conduit, and the insufflation conduit.

20. A method of operating a device to safely maintain a safely inflated state of a colon allowing internal observation during colon cleaning, the method comprising:
    evacuating material including fluid from the colon through a distal aperture of an evacuation conduit of the device inserted to a distal region of the colon, wherein the material is evacuated by suction supplied to the distal aperture;
    supplying irrigation fluid to the colon during the evacuating of the material through an irrigating subsystem comprising an irrigation conduit, and an irrigation source configured to supply the irrigation fluid comprising liquid through the irrigation conduit to the colon;
    sensing with a pressure sensor of the device a change in pressure measured within the distal region due to the evacuation of the material; and
    controlling, using a controller of the device, a supply of insufflating gas delivered to the colon from an insufflation conduit of an insufflation subsystem of the device comprising a gas source, and the insufflation conduit, wherein an amount of the supply of insufflating gas is determined automatically by the controller based on the sensed change in pressure
    wherein said irrigation conduit and said insufflation conduit are separate from one another; and
    wherein said evacuation conduit, said irrigation conduit, and said insufflation conduit are introducible into the colon; and
    wherein a colonoscope is configured to be introduced into the colon external to the insufflation conduit.

21. The method of claim 20, comprising adjusting the supply of insufflating gas, based on a relative proportion of gas in an evacuated mixture of at least gas and liquid.

22. The method of claim 20, wherein the amount of the supply of insufflating gas is also controlled by the controller based on an estimate of an amount of the material removed by a current rate of suction.

23. The method of claim 22, wherein the estimate of the amount of the material removed is based on a volume of the material removed by a positive displacement pump.

24. The method of claim 20, wherein a relative magnitude of a rate of the supply of insufflating gas compared to a magnitude of evacuation pressure supply is automatically decreased as the change in pressure measured increases.

25. A colon cleaning system for evacuating material from a distal end of a colon while keeping the colon in a safely inflated state allowing internal observation, the colon cleaning system comprising:
    an evacuation conduit having a distal region insertable to the colon to communicate suction for evacuating the material;
    an insufflation conduit for supply of insufflation gas to inflate the colon;
    an irrigating conduit, for supply of irrigating fluid to irrigate the colon;
    wherein said irrigating conduit and said insufflation conduit are separate from one another;
    a controller; and
    a pressure sensor configured to provide pressure measurements from the distal region to the controller;
    wherein the controller is configured to regulate a net flow of the supply of insufflation gas, the supply of irrigating fluid, and the suction to produce and maintain the safely inflated state, based on the pressure measurements; and
    wherein said evacuation conduit, said irrigating conduit, and said insufflation conduit are introducible into the colon; and
    wherein a colonoscope is configured to be introduced into the colon external to the insufflation conduit.

26. The colon cleaning system of claim 25, wherein the system comprises a sensor configured to measure a relative proportion of gas in an evacuated mixture of at least gas and liquid evacuated through the evacuation conduit; and wherein the controller is also configured to adjust the supply of insufflation gas, based on the relative proportion of gas in the evacuated mixture of at least gas and liquid.

* * * * *